(12) United States Patent
Zhu et al.

(10) Patent No.: US 12,257,364 B2
(45) Date of Patent: Mar. 25, 2025

(54) PREPARATION METHOD AND APPLICATION OF DECELLULARIZED EXTRACELLULAR MATRIX TISSUE PAPER

(71) Applicant: NANKAI UNIVERSITY, Tianjin (CN)

(72) Inventors: Meifeng Zhu, Tianjin (CN); Wen Li, Tianjin (CN); Deling Kong, Tianjin (CN); Zhen Zhang, Tianjin (CN)

(73) Assignee: NANKAI UNIVERSITY, Tianjin (CN)

( * ) Notice: Subject to any disclaimer, the term of this patent is extended or adjusted under 35 U.S.C. 154(b) by 0 days.

(21) Appl. No.: 18/122,009

(22) Filed: Mar. 15, 2023

(65) Prior Publication Data

US 2023/0405186 A1    Dec. 21, 2023

(30) Foreign Application Priority Data

May 31, 2022 (CN) .......................... 202210607526.0

(51) Int. Cl.
*A61L 27/36* (2006.01)

(52) U.S. Cl.
CPC ....... *A61L 27/3687* (2013.01); *A61L 27/3633* (2013.01); *A61L 2430/40* (2013.01)

(58) Field of Classification Search
CPC ............. A61L 27/3687; A61L 27/3633; A61L 2430/40
USPC ...................................................... 424/572
See application file for complete search history.

(56) References Cited

U.S. PATENT DOCUMENTS

| 2005/0013872 A1* | 1/2005 | Freyman | ................ A61K 35/28 514/9.2 |
| 2016/0053231 A1* | 2/2016 | Xu | ....................... A61L 27/3633 435/402 |

FOREIGN PATENT DOCUMENTS

| CN | 104208746 | * | 12/2014 |
| CN | 104740685 | A | 7/2015 |
| CN | 105903079 | * | 8/2016 |
| CN | 107254431 | A | 10/2017 |
| CN | 110038168 | A | 7/2019 |
| CN | 110975010 | A | 4/2020 |
| CN | 112138215 | A | 12/2020 |
| CN | 113289063 | * | 8/2021 |
| CN | 113694256 | A | 11/2021 |
| CN | 110975010 | * | 2/2022 |
| CN | 114191612 | A | 3/2022 |
| WO | 2013138864 | A1 | 9/2013 |
| WO | 2019055927 | A1 | 3/2019 |

\* cited by examiner

*Primary Examiner* — Jennifer M. H. Tichy

(57) ABSTRACT

The present disclosure discloses a preparation method and application of decellularized extracellular matrix tissue paper, and belongs to the technical field of regenerative medicine. The preparation method includes the following steps: (1) preparing decellularized extracellular matrix materials; (2) preparing tissue paper: homogenizing and stirring the prepared decellularized extracellular matrix materials, then, placing the obtained homogenates on a flat-bottom filter screen to filter out water, standing and air-drying the filtered homogenates, and freeze-drying the homogenates to obtain the tissue paper; (3) cross-linking the tissue paper: cross-linking the tissue paper in a cross-linking solution; and (4) freeze-drying or stacking and compacting the cross-linked tissue paper. According to the present disclosure, the decellularized extracellular matrix tissue paper with tissue specificity is prepared by a traditional paper-making technology combined with a freeze-drying technology.

7 Claims, 14 Drawing Sheets

| | Numbers of protein types |
|---|---|
| a | 1394 |
| b | 1320 |
| c | 1306 |
| d | 530 |

PREPARATION METHOD AND APPLICATION OF DECELLULARIZED EXTRACELLULAR MATRIX TISSUE PAPER

CROSS-REFERENCE TO RELATED APPLICATION

This application claims priority from the Chinese patent application 202210607526.0 filed May 31, 2022, the content of which are incorporated herein in the entirety by reference.

TECHNICAL FIELD

The present disclosure relates to the technical field of regenerative medicine, in particular to a preparation method and application of decellularized extracellular matrix tissue paper.

BACKGROUND ART

Biomaterials can be used to replace and repair injured and degenerated tissue. The biomaterials should be of a suitable pore structure to provide a physical, structural support for the growth of cells and tissue, and meanwhile, have high biocompatibility, bioactivity and excellent mechanical properties. Decellularized extracellular matrix (dECM) materials refer to extracellular matrix materials obtained by decellularizing organs/tissue of human bodies or animals to remove cells and immunogenic components. The dECM materials retain physical and chemical properties and a large number of extracellular matrix components, such as collagen, elastin, proteoglycan and glycosaminoglycan, and so on. Compared with commonly used native or synthetic materials, the dECM may provide a micro-environment similar to native tissue for regeneration and repair of the injured tissue. A large number of studies showed that the dECM materials may promote tissue regeneration and repair by regulating the immune response. At present, a variety of products made of the dECM materials, such as bovine pericardium, pig skin and small intestinal submucosa, have been applied in clinic, which indicated that the dECM materials had broad application prospects.

However, such products commonly used in clinicare generally obtained by directly cross-linking the obtained tissue after the decellularization of the acquired tissue, and are lack controllability for macro and micro structures of the materials. Meanwhile, such products are compact in structure, which may limit cell migration and tissue regeneration. To solve the problems, many studies have been done to improve the properties of the dECM materials by introducing various processes, such as electrostatic spinning, 3D printing, hydrogel, microencapsulation and microcarriers. However, it is necessary to dissolve or digest the dECM with acids, enzyme solutions, or organic solvents in the above processes. Consequently, the extracellular matrix components are damaged or lost to reduce the bioactivity thereof.

The patent CN110038168A has provided a muscle tendon anti-adhesion film prepared from dECM. In such technical solution, decellularized tendon tissue needed to be dissolved in an acetic acid solution after being crushed, and then the obtained solution was neutralized by a NaOH solution. The patent CN113713165A has provided a preparation method of dECM fiber sponge. In such technical solution, the dECM also need to be mixed with an acetic acid and water. However, the use of acetic acid may damage the extracellular matrix components and activity.

Therefore, existing technical solutions for preparing the dECM materials have apparent shortcomings. It is necessary to develop a novel green and mild preparation process which can effectively retain the extracellular matrix components and activity.

SUMMARY

The present disclosure aims to provide a preparation method and application of dECM tissue paper to solve the above problems in the prior art. In this method, no acids, enzymes, or organic solvents are used, and the ECM components and activity may be retained to a maximum extent. The preparation is simple, and industrial production is easy to achieve.

To achieve the above objectives, the present disclosure provides the following solution:

The present disclosure provides a preparation method of dECM tissue paper, including the following steps:
(1) preparing dECM materials: taking fresh tissue for decellularizing after disinfecting and sterilizing to obtain the dECM materials;
(2) preparing tissue paper: homogenizing and stirring the dECM, then, placing the obtained homogenates on a flat-bottom filter screen to filter out water, standing and air-drying the filtered homogenates, and then freeze-drying the homogenates to obtain the tissue paper;
(3) cross-linking the tissue paper: cross-linking the tissue paper obtained in step (2) in a cross-linking solution; and
(4) freeze-drying or stacking and compacting the cross-linked tissue paper, to obtain the dECM tissue paper.

Furthermore, decellularizing includes steps of slicing the fresh tissue after being washed, washing the tissue by adding sterilized water or normal saline after being disinfected with peroxyacetic acid, and then washing the washed tissue with a buffer containing DNase and RNase.

Furthermore, in step (2), the homogenizing and stirring time ranges from 1 minute to 60 minutes, the size of the flat-bottom filter screen ranges from 3 meshes to 500 meshes, the standing and air-drying time ranges from 1 hour to 120 hours, the freeze-drying temperature ranges from −196° C. to −20° C., and time ranges from 4 hours to 48 hours.

Furthermore, the cross-linking solution in step (3) is an ethanol solution containing a cross-linking agent; the cross-linking agent includes one or more of 1-ethyl-(3-dimethylaminopropyl) carbonyldiimine, N-hydroxysuccinimide, glutaraldehyde, formaldehyde and genipin.

Furthermore, the cross-linking is conducted at the temperature ranges from 4° C. to 27° C. for 4 hours to 12 hours.

Furthermore, the freeze-drying temperature in step (4) ranges from −196° C. to −20° C., and time ranges from 12 hours to 72 hours.

Furthermore, fresh tissue includes tissue or organs of a human body or an animal.

Furthermore, the fresh tissue includes the cerebrum, heart, liver, spleen, lungs, kidneys, skin, fat, meninges, diaphragm, amnion, pericardium, heart valves, small intestine submucosa, muscles, blood vessels, tendons, ligaments, cartilage, esophagus, trachea, stomach, nerves, bladder, cornea and/or placenta.

The present disclosure further provides the dECM tissue paper prepared by the preparation method.

Furthermore, according to the present disclosure, the dECM tissue paper with tissue specificity is prepared by a traditional paper-making technology combined with a freeze-drying technology and other technologies. No acids, enzymes or organic solvents are used during the processing of the dECM, the process is mild, and therefore native extracellular matrix components and activity may be retained to a maximum extent. The obtained dECM tissue paper has some properties of paper, and can be curled, folded, sutured, clipped and the like. In addition, the mechanical properties of the tissue paper may be further improved by a cross-linking reaction or stacking and compacting of multiple layers of tissue paper.

The present disclosure further provides an application of the dECM tissue paper in the preparation of drugs for repairing injured tissue.

The present disclosure has the following technical effects:
1. The acids, enzyme dissolution or addition of the organic solvents is involved in the conventional processing of the dECM materials and consequently the components and activity thereof are damaged. In the dECM processing method adopted in the present disclosure, no acids, enzymes or organic solvents are used, and the ECM components and activity can be retained to a maximum extent; and the preparation is simple, and the industrial production is easy to achieve.
2. Existing pure dECM materials are compact in structure and low in mechanical strength and poor in controllability. Consequently, the effect in promoting tissue repair of the dECM materials can be limited. According to the present disclosure, the extracellular matrix tissue paper with controllable thickness, pore diameter and mechanical strength can be prepared by obtaining the dECM materials from different tissue sources and regulating the usage amount, homogenizing time, air-drying time, freezing temperature, cross-linking time and the like of the decellularized tissue. Meanwhile, the tissue paper structure can be regulated according to clinical needs, and the mechanical properties of the tissue paper are enhanced to expand the application range of the tissue paper.

BRIEF DESCRIPTION OF THE DRAWINGS

In order to more clearly explain the technical solutions in embodiments of the present disclosure or the prior art, drawings required to be used in the embodiments will be briefly described below, apparently the drawings in the following description are only some embodiments of the present disclosure, and a person of ordinary skill in the art can also obtain other drawings according to these drawings without involving creative work.

FIG. 1A: Venn diagram of protein samples treated by different methods; FIG. 1B: statistical results of numbers of protein types in ECM samples treated by different methods; wherein a, b, c, and d represent native heart tissue, decellularized heart tissue, decellularized heart tissue paper and decellularized heart tissue digested by acetic acid and enzymes;

FIGS. 2A-2D illustrate mass spectrograms of different samples after treatment by different methods; wherein, FIG. 2A: native heart tissue; FIG. 2B: decellularized heart tissue; FIG. 2C: decellularized heart tissue paper; and FIG. 2D: decellularized heart tissue dissolved by acids and enzymatically hydrolyzed;

FIGS. 3A-3C illustrates representation diagrams of structural morphology of dECM products in Embodiments 1 to 4 and Comparative Example 2; wherein, FIG. 3A: Macro morphology and microstructure pictures; FIG. 3B: Statistical graph of pore diameters of porous structures; FIG. 3C: Statistical graph of porosity;

FIGS. 4A-4C illustrates the evaluation of mechanical properties of tissue paper from four tissue sources in Embodiments 1 to 4; wherein, FIG. 4A: Stress-strain curves of four types of tissue paper; FIG. 4B: Tensile strength statistics of four types of tissue paper; FIG. 4C: Suture strength statistics of four types of tissue paper;

FIGS. 5A-5C illustrates the evaluation of cell compatibility of tissue paper from four tissue sources in Embodiments 1 to 4; wherein, FIG. 5A: Live and dead cell staining of mesenchymal stem cells after culture on the tissue paper for 1 day on the tissue paper; FIG. 5B: Statistical graph of cell survival rates; FIG. 5C: Statistical graph of the proliferation of stem cells tested by a cell counting kit 8 (CCK8) in tissue paper leaching liquor.

DETAILED DESCRIPTION OF THE PRESENT DISCLOSURE

Figures 1A, 1B:
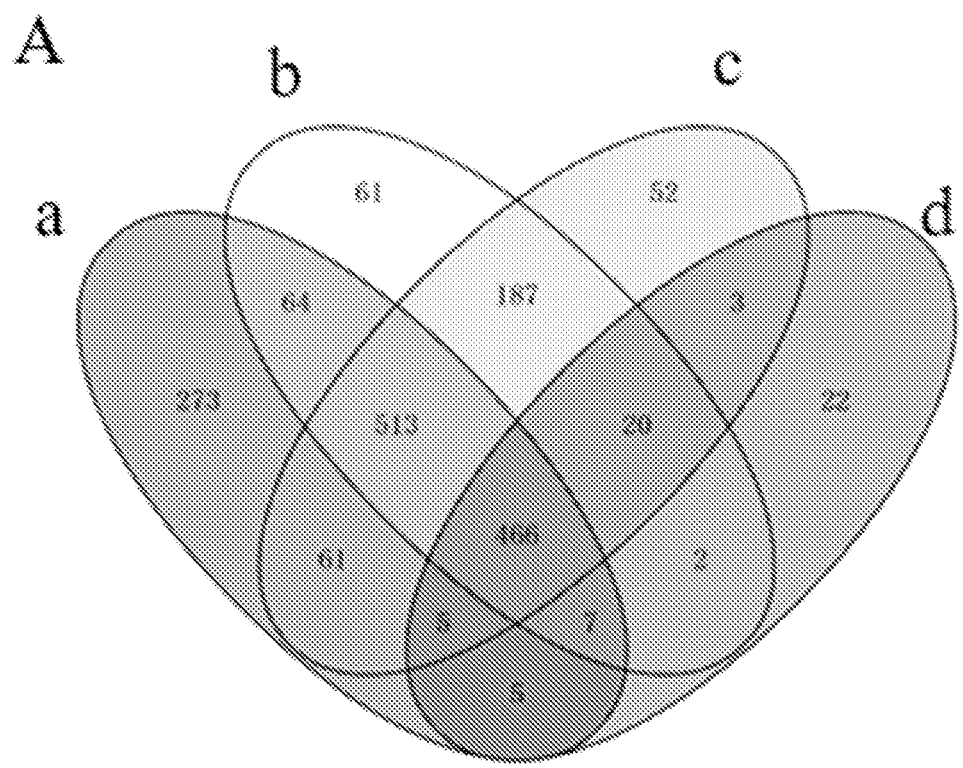
FIGS. 1A-1B illustrate statistics of ECM protein types after treatment by different methods.

Various exemplary implementations of the present disclosure will be described in detail below, which should not be construed as limiting the present disclosure, but as a more detailed description of certain aspects, features, and implementation solutions of the present disclosure.

It should be understood that the terms used in the present disclosure are for the purpose of describing particular implementations only and are not intended to limit the present disclosure. In addition, for a numerical range in the present disclosure, it should be understood that each median value, between the upper and lower limits of that range, is also specifically disclosed. Each smaller range between any stated value or median value in the stated range and any other stated values or median value in the stated range is also included within the present disclosure. The upper and lower limits of these smaller ranges may be independently included in or excluded from the range.

Unless otherwise indicated, all technical and scientific terms used herein have the same meaning as commonly understood by those ordinarily skilled in the art to which the present disclosure belongs. Although only preferred methods and materials are described in the present disclosure, any methods and materials similar or equivalent to those described herein can be used in the implementation or test of the present disclosure. All documents mentioned in this specification are hereby incorporated by reference for the purpose of disclosing and describing the methods and/or materials associated with the documents. In case of conflict with any incorporated document, the content of the specification will prevail.

It will be apparent to those skilled in the art that various modifications and variations can be made to the specific implementations of the specification of the present disclosure without departing from the scope or spirit of the present disclosure. Other implementations obtained according to the specification of the present disclosure will be apparent to those skilled in the art. The specification and embodiments of the present disclosure are intended to be illustrative only.

As used herein, the terms "comprising", "including", "having", "containing", and the like are open-ended terms that mean including, but not limited to.

Unless otherwise specified, materials, instruments, and reagents used in the present disclosure are commercially available; unless otherwise specified, experimental methods used are conventional experimental methods in the art.

Embodiment 1 Preparation of Porcine Heart Tissue Paper

Preparation of decellularized heart tissue: purchased fresh porcine heart tissue is cut into slices with thickness of 1 mm after being washed thoroughly, and filled into a glass bottle; and after disinfection and sterilization with 0.1% peroxyacetic acid, sterilized water is added for shaking and washing on a shaker, till the solution becomes clear, a 1% sodium dodecyl sulfate (SDS) solution is added for shaking and washing for 72 hours, and the solution is changed once every three hours, till the tissue becomes white. Then, the tissue is washed with the sterilized water to remove the residual SDS, and shaken on the shaker with a Tris-HCL buffer with DNase I and RNase added at 37° C. and 100 rpm for 24 hours to remove DNA and RNA from the tissue. Finally, the tissue is washed with the sterilized water to obtain porcine heart extracellular matrix materials.

Preparation of porcine heart extracellular matrix tissue paper (HTP): 10 g of porcine heart decellularized tissue is weighted on a wet weight basis, 100 mL of distilled water is added to the decellularized tissue, the mixture is smashed in a homogenizer for a set time of 10 minutes, to obtain homogenates, then the homogenates are poured into a 300-mesh flat-bottom filter screen with a diameter of 8 cm for standing to filter out water and air-dried at room temperature for 48 hours, and then the dried homogenates are frozen in a refrigerator at −80° C. for 4 hours, and finally transferred into a freeze dryer for freeze-drying for 48 hours, to obtain decellularized heat tissue paper. The porcine heart extracellular matrix tissue paper with different thicknesses and pore diameters may be prepared by regulating the amount of porcine heart extracellular matrices, a mesh number of the filter screen, air-drying time, and the like.

Tissue paper cross-linking: firstly, 100 mL of 80% ethanol solution is prepared, 1-ethyl-(3-dimethylaminopropyl) carbonyldiimine (EDC) and N-hydroxysuccinimide (NHS) are added to the ethanol solution at a mass ratio is 4:1 to prepare a solution with a concentration of 0.3%, and a cross-linking solution is obtained. Then, the porcine heart extracellular matrix tissue paper is immersed into the solution for cross-linking at 4° C. for 10 hours, then taken out, soaked, and washed with the sterilized water several times to remove the residual cross-linking agent.

Freeze drying: the cross-linked and washed tissue is frozen in the refrigerator at −20° C. for 12 hours, and then freeze-dried in the freeze dryer for 48 hours, to obtain a finished product of the porcine heart extracellular matrix tissue paper with higher mechanical strength. A plurality of pieces of porcine heart tissue paper may be further stacked and compacted for later use.

Embodiment 2 Preparation of Porcine Liver Tissue Paper

Preparation of decellularized liver tissue: a purchased fresh porcine liver is cut into slices with thickness of 1 mm after being washed thoroughly, and filled into a glass bottle; after disinfection and sterilization with 0.1% peroxyacetic acid, sterilized water is added for shaking and washing on a shaker, till the solution becomes clear, a 1% SDS solution is added for shaking and washing for 24 hours, and the solution is changed once every three hours, till the tissue becomes white. Then, the tissue is washed with the sterilized water to remove the residual SDS, then placed in a Tris-HCL buffer containing 50 U/mL of DNase and 1 U/mL of RNase, and shaken on a shaker at 37° C. and 100 rpm for 24 hours to erase DNA and RNA from the tissue. Finally, the tissue is washed with the sterilized water to remove enzymes, to obtain porcine liver extracellular matrix materials.

Preparation of porcine liver extracellular matrix tissue paper (LTP): 30 g of porcine liver extracellular matrix materials are weighted on a wet weight basis, placed in a homogenizer and stirred for 5 minutes to obtain homogenates, and then the homogenates are poured into a 200-mesh flat-bottom filter screen with a diameter of 10 cm for standing to filter out water, and air-dried at room temperature for 10 hours. Then, the air-dried homogenates are frozen in a refrigerator at −20° C. for 12 hours, transferred into a freeze dryer and freeze-dried for 36 hours, to obtain the porcine liver extracellular matrix tissue paper. The porcine liver tissue paper with different thicknesses may be prepared by regulating the amount of porcine liver extracellular matrices.

Tissue paper cross-linking: the freeze-dried porcine liver extracellular matrix tissue paper is taken and placed in an 80% ethanol solution containing EDC/NHS with a mass ratio of 4:1, and cross-linked at 4° C. for 12 hours; and after being taken out, the tissue paper is soaked and washed with sterilized water for 5 times to remove the residual cross-linking reagent.

Freeze drying: the cross-linked and washed porcine liver extracellular matrix tissue paper is frozen at −80° C. for 4 hours, and freeze-dried in the freeze dryer for 36 hours, to obtain a finished product of the porcine liver extracellular matrix tissue paper with enhanced mechanical properties, and a plurality of pieces of porcine liver extracellular matrix tissue paper may be further stacked and compacted for later use.

Embodiment 3 Preparation of Porcine Kidney Tissue Paper

Preparation of decellularized kidney tissue: a purchased fresh porcine kidney is cut into small slices with a thickness of 1 mm after being washed thoroughly, and filled into a glass bottle; and after disinfection and sterilization with 0.1% peroxyacetic acid, sterilized water is added for shaking and washing on a shaker, till the solution becomes clear, a 1% SDS solution is added for shaking and washing for 48 hours, and the solution is changed once every three hours, till the tissue becomes white. Then, the tissue is washed with the sterilized water to remove the residual SDS, then the tissue is washed with a Tris-HCL buffer with DNase and RNase added for overnight at the temperature of 37° C., to erase DNA and RNA from the tissue, and finally the tissue is washed with the sterilized water to obtain porcine kidney extracellular matrix materials.

Preparation of porcine kidney extracellular matrix tissue paper (KTP): 20 g of pig kidney decellularized tissue is weighted on a wet weight basis, 200 mL of distilled water is added to the decellularized tissue, the mixture is smashed in a homogenizer for 10 minutes, to obtain homogenates, then the obtained homogenates are poured into a 200-mesh flat-bottom filter screen with a diameter of 10 cm for standing to filter out water and air-dried at room temperature for 72 hours, then the dried homogenates are placed in a refrigerator at −20° C. for 12 hours, and finally transferred into a freeze dryer for freeze-drying for 48 hours, to obtain the porcine kidney extracellular matrix tissue paper.

Tissue paper cross-linking: firstly, 100 mL of 80% ethanol solution is prepared, EDC and NHS, are added to the ethanol solution at a mass ratio is 4:1 to prepare a solution with an EDC concentration of 0.3%, and a cross-linking solution is obtained. Then, the kidney extracellular matrix tissue paper is immersed into the solution for cross-linking at room temperature for 4 hours, then taken out, soaked and washed with the sterilized water for several times to remove the residual cross-linking reagent.

Freeze drying: the cross-linked and washed tissue paper is frozen in the refrigerator at −80° C. for 4 hours, and then freeze-dried in the freeze dryer for 48 hours, to obtain a finished product of the porcine kidney extracellular matrix tissue paper with higher mechanical strength. A plurality of porcine kidney extracellular matrix tissue paper may be further stacked and compacted for later use.

Embodiment 4 Preparation of Tendon Tissue Paper

Preparation of decellularized tendon tissue: fresh porcine tendon tissue is taken, and cut into slices with a thickness of about 500 μm after the surrounding connective tissue is removed; after disinfection and sterilization with 0.1% peroxyacetic acid, the tissue is washed with sterilized water, immersed in liquid nitrogen for 2 minutes, then placed into 400 mL of normal saline and shaken on a shaker at 37° C. and 100 rpm for 15 minutes, and frozen and thawed repeatedly for 5 times. In order to remove residual cell nuclei, after the tissue is washed for the last time, the sample is placed in a reaction mixture containing 50 U/mL of DNase I and 1 U/mL of RNase A, and reacts on a shaker at 37° C. and 100 rpm for 24 hours. Then, the sample is washed with sterile PBS to remove enzyme solutions, to obtain the decellularized tendon tissue.

Preparation of porcine tendon extracellular matrix tissue paper (TTP): 50 g of porcine tendon decellularized tissue is weighted on a wet weight basis, placed into a homogenizer and smashed for 30 minutes, to obtain homogenates, then the obtained homogenates are poured into a 200-mesh flat-bottom filter screen with a diameter of 10 cm for standing to filter out water, and air-dried at room temperature for 36 hours, and then the dried homogenates are freeze-dried in a freeze dryer for 24 hours after being quickly frozen in liquid nitrogen, to obtain the tendon extracellular matrix tissue paper.

Tissue paper cross-linking: the freeze-dried porcine tendon extracellular matrix tissue paper is taken and placed in an 80% ethanol solution containing EDC/NHS with a mass ratio of 4:1, cross-linked at 4° C. for 12 hours, and taken out on the next day, and then the cross-linked tissue paper is soaked and washed with the sterilized water for several times to remove the residual cross-linking reagent.

Freeze drying: the cross-linked and washed tendon extracellular matrix tissue paper is frozen at −80° C. for 4 hours, then quickly transferred to a pre-cooled freeze dryer to perform freeze-drying for 36 hours, to obtain a finished product of the porcine tendon extracellular matrix tissue paper, and a plurality of pieces of porcine tendon extracellular matrix tissue paper may be further stacked and compacted for later use.

Comparative Example 1

The difference between comparative example 1 and Embodiment 1 lies in that the porcine heart decellularized matrix materials are subjected to cross-linking after being dissolved and digested by an acetic acid and pepsin and cast into membranes.

Comparative Example 2

The difference between comparative example 2 and Embodiment 1 lies in that the comparative example 2 being prepared without the preparation process of the decellularized extracellular matrix tissue paper.

Effective Example 1

Figure 2A:
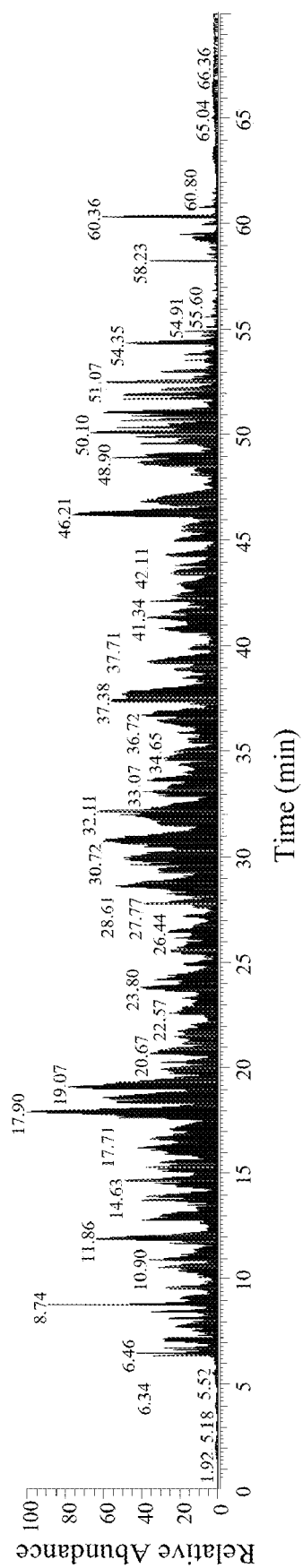
Figure 2B:
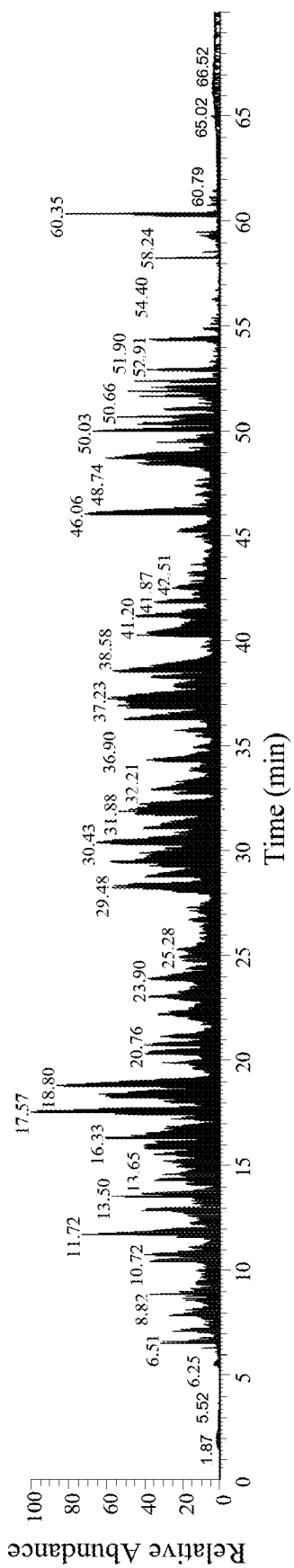
Figure 2C:
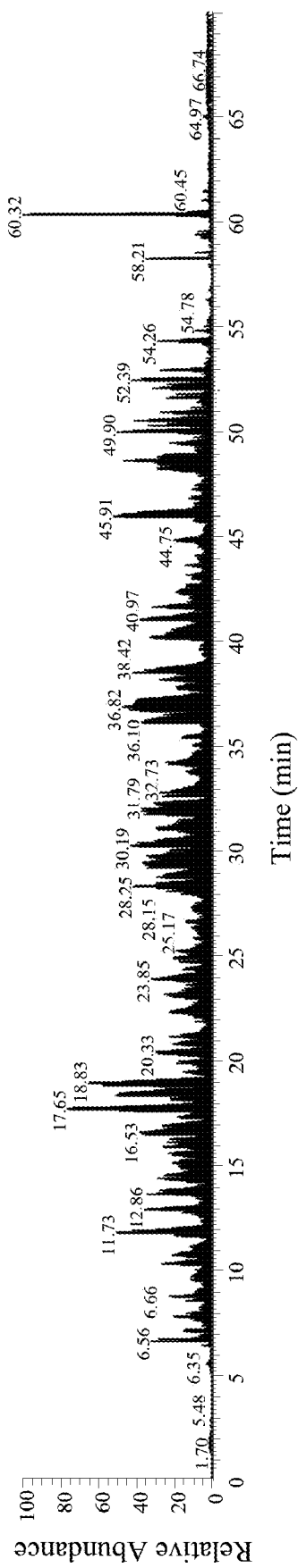
Figure 2D:
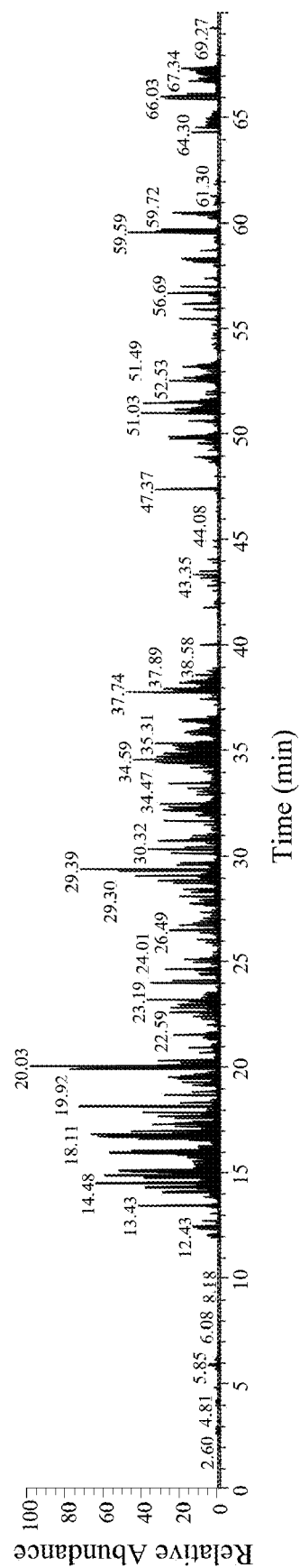

By taking porcine heat tissue as an example, numbers of protein types and abundance of peptide segments in samples of porcine-derived native heart tissue, decellularized heart tissue (Comparative Example 2), decellularized heart tissue paper (Embodiment 1) and decellularized heart tissue (Comparative Example 1) dissolved and digested by an acetic acid and pepsin were tested by proteomics respectively.
Test Method:

The matrix composition of four heart tissue samples treated differently was tested by a proteomic method. A protein identification process includes the main steps: protein enzymolysis, LC-MS/MS analysis, database retrieval, data analysis, and the like. This test was completed by Shanghai BIOPROFILE Co., Ltd., and an experimental result report was obtained. The experimental results were shown in FIGS. 1A-2B and FIGS. 2A-2D:

FIGS. 1A-1B is a statistical graph of protein types after treatment to ECM by different methods, FIG. 1A: Venn diagram of protein types samples treated by different methods; FIG. 1B: statistical results of numbers of protein types in ECM samples treated by different methods; wherein a, b, c and d represent the native heart tissue, the decellularized heart tissue, the decellularized heart tissue paper and the decellularized heart tissue digested by the acetic acid and enzymes. FIGS. 2A-2D illustrates mass spectrograms of heat tissue samples after treatment to ECM by different methods; FIG. 2A: native heart tissue; FIG. 2B: decellularized heart tissue; FIG. 2C: decellularized heart tissue paper; and FIG. 2D: decellularized heart tissue dissolved by acetic acid and enzymatically hydrolyzed.

It can be seen from FIGS. 1A-1B that the number of the protein types in the decellularized heart tissue paper is slightly lower than that of the native heart tissue, and slightly differs from that of the decellularized heart tissue, which shows that the preparation process of the decellularized ECM tissue paper may properly retain the original components of the ECM tissue. However, by using the treatment method of acid dissolution and enzymolysis, the number of the protein types in the decellularized heart tissue is decreased by 900 or so, and the components of the ECM materials are damaged severely. It can be known from FIGS. 2A-2D that the peptide fragment peaks of the native heart tissue, the decellularized heart tissue and the decellularized heart tissue paper are basically consistent, which indicates that there is no significant difference among protein components, and both the peak position and peak intensity in samples dissolved by acids and enzymatically hydrolyzed significantly differ from those of the native tissue. It can be obtained that compared with a traditional processing method of acid dissolution and enzymolysis, the preparation process of the decellularized extracellular matrix tissue paper in the present disclosure may better retain native extracellular matrix components.

Effective Example 2

The representation of structural morphology of the decellularized extracellular matrix products (heart matrix, liver matrix, kidney matrix and tendon matrix) prepared according to Embodiments 1 to 4 and by the conventional preparation method of the decellularized extracellular matrix of the Comparative Example 2 in the present disclosure was tested.

Test Process:

The macro morphologies of four types of prepared tissue paper and four conventional decellularized extracellular matrices were photographed and observed, and the microstructures of the tissue paper surfaces and decellularized extracellular matrix products were photographed and recorded carefully by using a scanning electron microscope (SEM) under accelerating voltage of 15 kV after metal spraying of the surfaces. Finally, the pore diameter of the tissue paper was measured by using Image J software, and the porosity of the tissue paper materials was determined by a liquid immersion method.

Figure 3A:
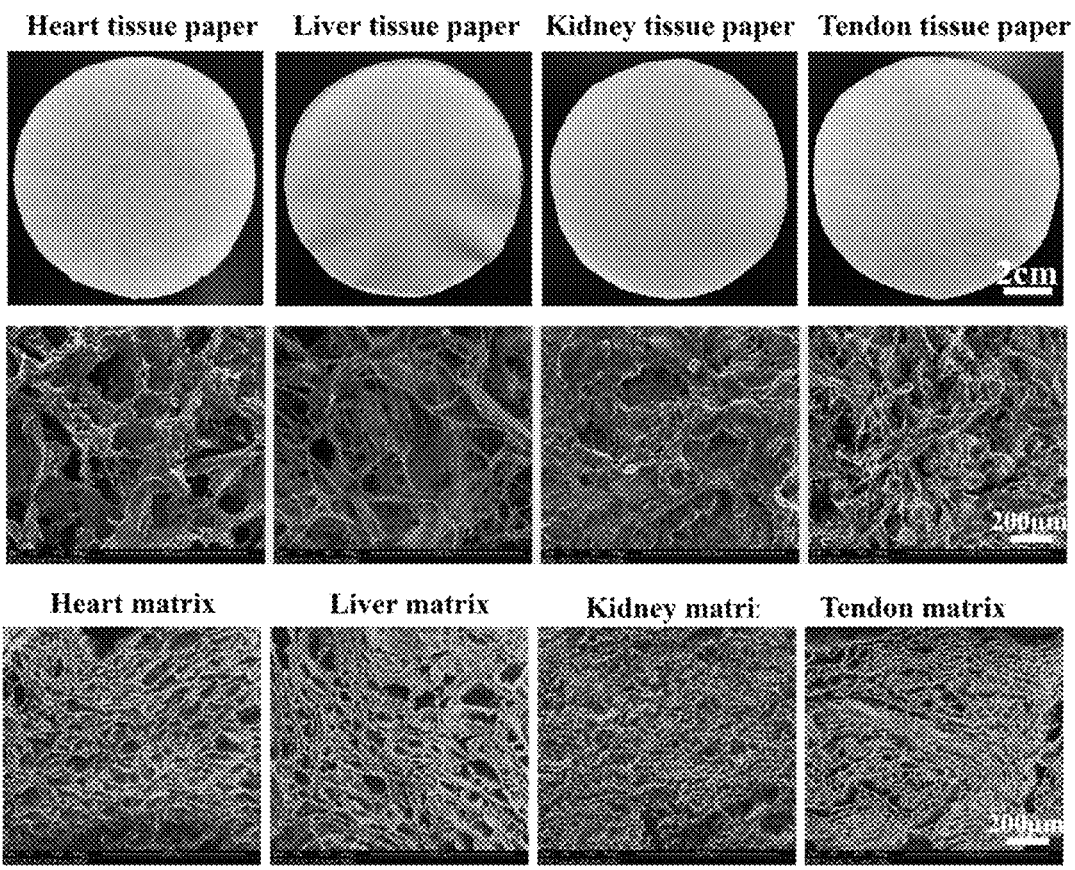
Figure 3B:
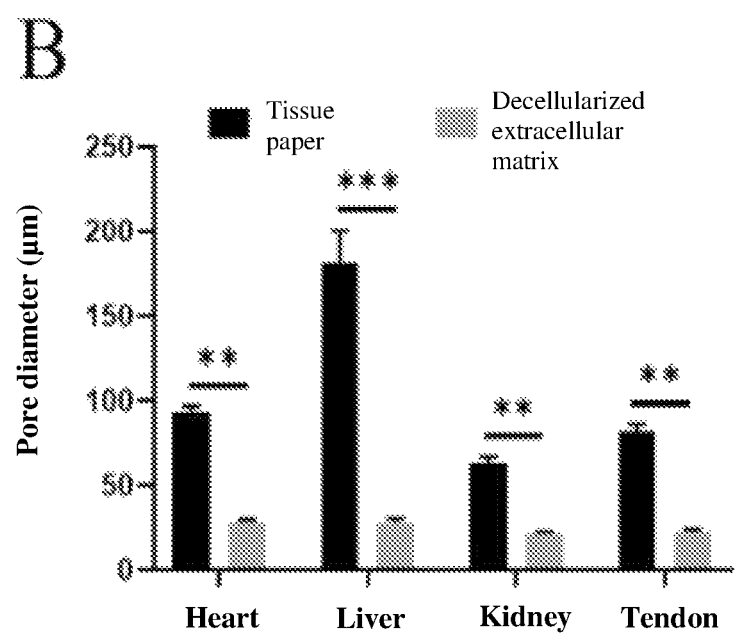
Figure 3C:
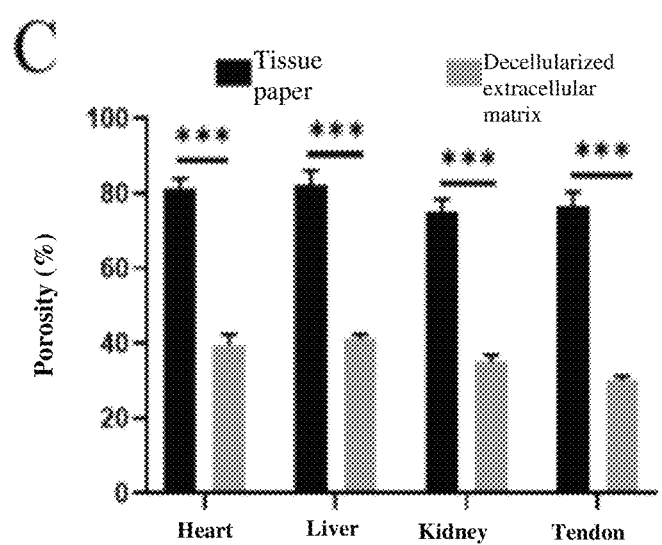

In FIGS. 3A-3C, FIG. 3A illustrates macro morphologies and microstructure pictures of decellularized extracellular matrix tissue paper prepared in Embodiments 1 to 4 and conventional decellularized extracellular matrix products; FIG. 3B: Statistical graph of pore diameters of porous structures of four types of decellularized extracellular matrix tissue paper and four conventional decellularized extracellular matrix surfaces; FIG. 3C: Statistical graph of porosities of four types of decellularized extracellular matrix tissue paper and four conventional decellularized extracellular matrices.

It can be seen from FIGS. 3A-3C that the tissue paper prepared in Embodiments 1 to 4 of the present disclosure is very similar to "paper" in terms of macro morphologies, and has a rich porous structure in microstructure. The tissue paper from different tissue sources has large pore diameters and higher porosities, thereby benefiting cell infiltration and promotion of tissue regeneration. The decellularized extracellular matrix materials prepared according to the method in Comparative Example 2 are more compact in microstructure, smaller in pore diameter and lower in porosity, which may limit cell migration and tissue regeneration.

Effective Example 3

Performance evaluation of decellularized extracellular matrix tissue paper prepared by the present disclosure
1. Mechanical Properties Evaluation
Test Method:

The tissue paper was cut into rectangular pieces with dimensions of 3 cm×l cm, and the mechanical properties of the tissue paper were measured by a uniaxial mechanical extensometer. A tensile parameter was set to 10 mm/min, and the tissue paper was longitudinally stretched to obtain tensile stress and a stress-strain curve. Suture strength test: the tissue paper with a length of 2 cm was cut, one end of the tissue paper was fixed to one side of a tensile testing machine, and the other end of the tissue paper was fixed to the other side of the tensile testing machine by inserting a suture 6-0 at a position 2 mm away from a tail end of the tissue paper and tying a knot; and the tissue paper was stretched at a speed of 10 mm/min till the tissue paper was broken, and the obtained maximum load is the suture strength of the tissue paper.

Figure 4A:
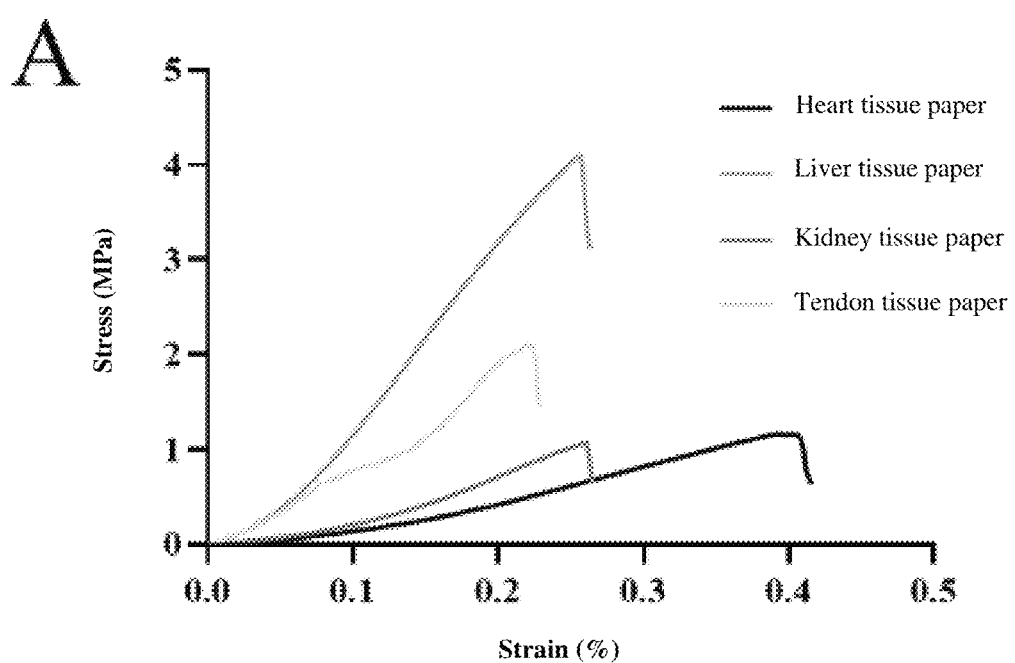
Figure 4B:
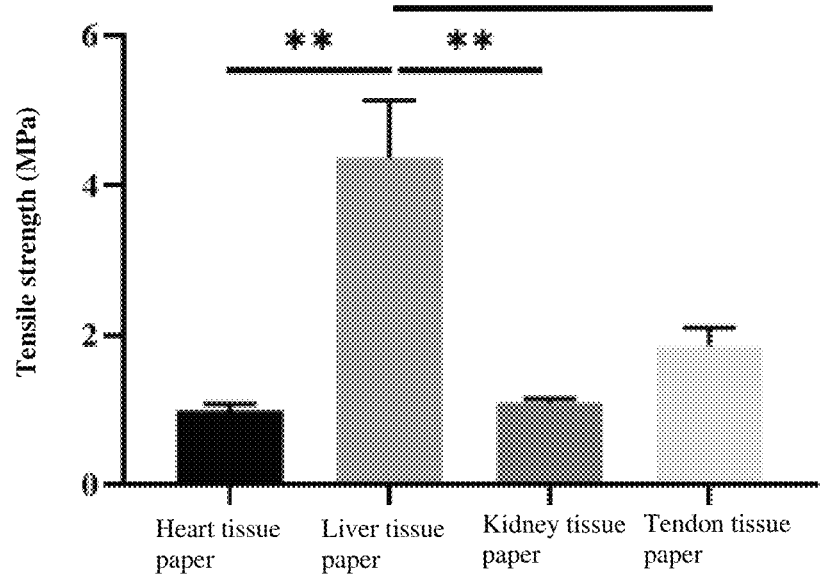
Figure 4C:
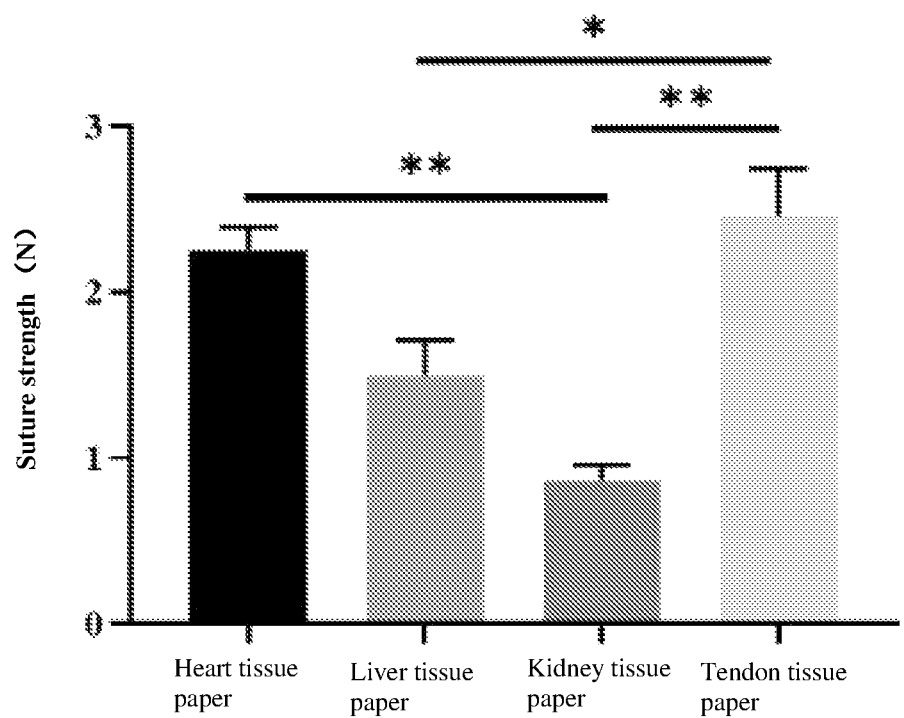

FIGS. 4A-4C illustrates the evaluation of mechanical properties of the tissue paper in Embodiments 1 to 4; wherein FIG. 4A shows stress-strain curves of four types of tissue paper; FIG. 4B shows tensile strength statistics of four types of tissue paper; and FIG. 4C shows suture strength statistics of four types of tissue paper.

It can be seen from FIGS. 4A-4C that all four types of tissue paper from different sources are higher in mechanical strength, the maximum stress is more than 1 Mpa, wherein the mechanical strength of the liver tissue paper is maximal. In addition, all the tissue paper also has sufficient suture strength. Therefore, the prepared tissue paper may well meet the requirements for mechanical and suture strength during in vivo application.

2. Evaluation of Cell Compatibility
Test Method:

$4 \times 10^4$ stem cells were implanted on a tissue paper membrane in a 48-well plate, and cultured for 24 hours, then a culture solution was pipetted, Calcein AM and PI live and dead cell staining solutions were added, the stem cells were incubated in the dark at room temperature for 20 minutes, and observed and photographed by a confocal microscope, and the numbers of live and dead cells and the survival rate were counted.

In the cell proliferation assay, firstly, 0.1 g of tissue paper was soaked in 5 ml of culture medium and incubated for 24 hours to obtain a tissue paper leaching liquor. Then, the stem cells were inoculated into a 96-well plate at $3 \times 10^3$ cells/well, 100 μl of leaching liquor was added for culture, the well plate was taken out on Day 1, Day 3 and Day 5 respectively, 10 μl of CCK8 working solution was added, the stem cells were incubated at 37° C. for 2 hours, and an absorbance was tested by a microplate reader.

Figure 5A:
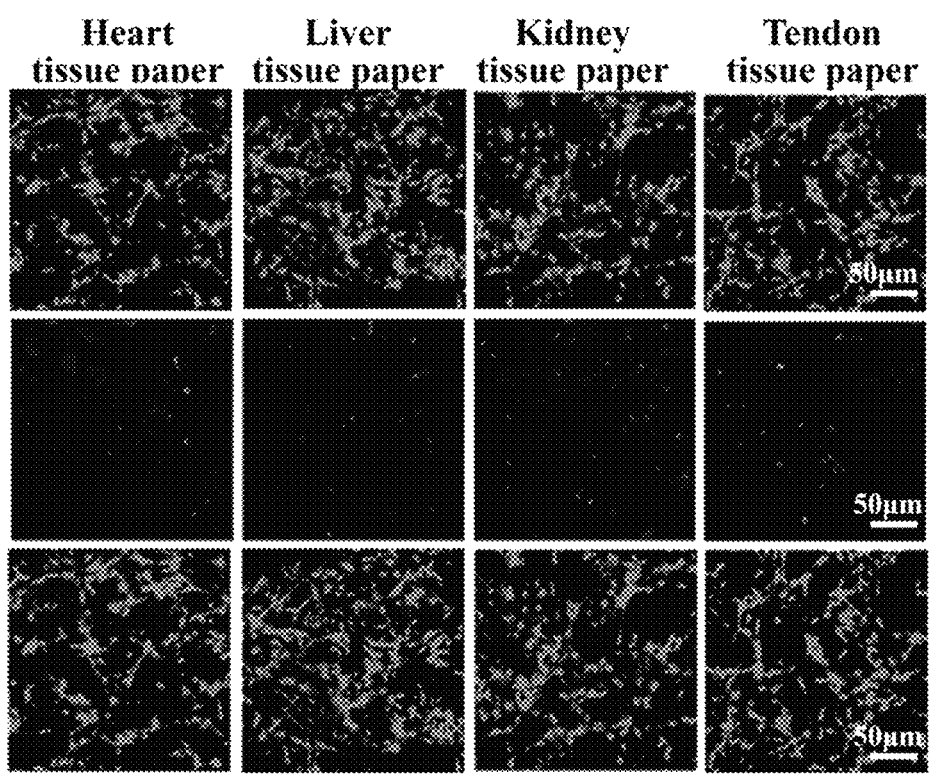
Figure 5B:
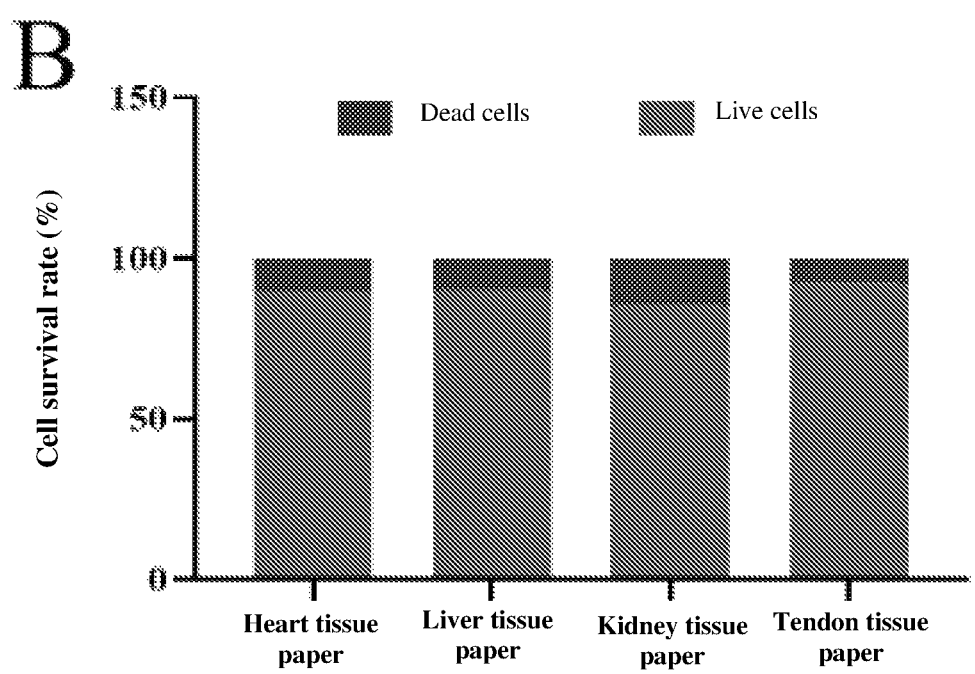
Figure 5C:
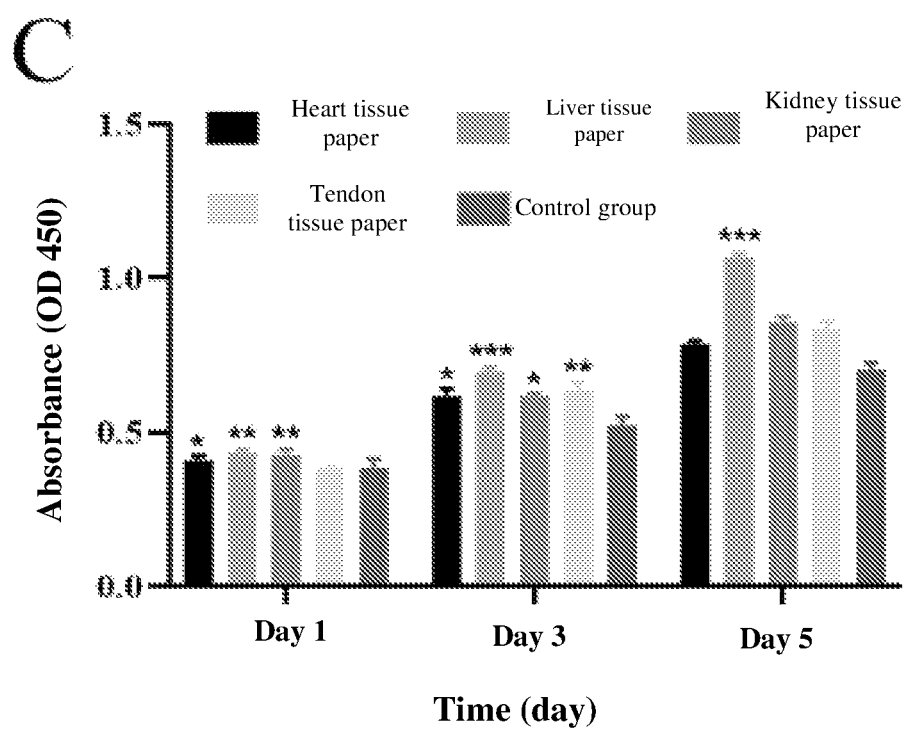

FIGS. 5A-5C illustrates cell compatibility of four types of decellularized extracellular matrix tissue paper; wherein FIG. 5A shows live and dead cell staining after mesenchymal stem cells are cultured on the tissue paper for 1 day; FIG. 5B shows statistical graph of cell survival rates; FIG. 5C shows proliferation of the stem cells tested by CCK8 in the tissue paper leaching liquor.

It can be seen from FIGS. 5A-5C that the extracted mesenchymal stem cells were properly adhered to and spread on the four types of tissue paper, the cell survival rate was 90%, which showed that the tissue paper had high cell compatibility. In addition, compared with a blank culture medium, the culture in the tissue paper leaching liquor significantly promoted the proliferation of the stem cells, which showed that the tissue paper had high bioactivity.

The above-described embodiments are merely a description of preferred modes of the present disclosure, and are not construed as limiting the scope of the present disclosure. Various modifications and improvements made by those ordinarily skilled in the art to the technical solutions of the present disclosure without departing from the spirit of the design of the present disclosure should fall within the protection scope defined by the claims of the present disclosure.

What is claimed is:

1. A preparation method of decellularized extracellular matrix tissue paper, comprising the following steps:
    (1) preparing decellularized extracellular matrix materials, comprising:
        washing a tissue with water and then slicing the tissue;
        disinfecting the washed sliced tissue with a peroxyacetic acid;
        washing the disinfected tissue by adding sterilized water or normal saline; and further washing the disinfected tissue with a buffer containing DNase and RNase so as to remove DNA and RNA;

(2) preparing tissue paper, comprising:

homogenizing and stirring the decellularized extracellular matrix materials from step (1) for a time ranging from 1 minute to 60 minutes to obtain a homogenate;

placing the obtained homogenate on a flat-bottom filter screen to filter out water from the obtained homogenate to obtain filtered homogenate, wherein the water passes through the flat-bottom filter screen, and air-drying the filtered homogenate on the flat-bottom filter screen to obtain air-dried homogenate, wherein placing the obtained homogenate on the flat-bottom filter screen and air-drying the filtered homogenate is performed in a range of from 1 hour to 120 hours; and freeze-drying the air-dried homogenate at a temperature ranging from −196° C. to −20° C. for 4 hours to 48 hours, to obtain the tissue paper (3) cross-linking the tissue paper, comprising:

cross-linking the tissue paper obtained in step (2) in a cross-linking solution, wherein the cross-linking solution in step (3) is an ethanol solution containing a cross-linking agent, the cross-linking agent comprising one or more of 1-ethyl-(3-dimethylaminopropyl) carbonyldiimine, N-hydroxysuccinimide, glutaraldehyde, formaldehyde, and genipin, and wherein the cross-linking is conducted at a temperature of 4° C. to 27° C. for 4 hours to 12 hours; and (4) freeze-drying the cross-linked tissue paper, comprising:

freeze-drying the cross-linked tissue paper obtained in step (3), to obtain the decellularized extracellular matrix tissue paper, wherein the freeze-drying temperature in step (4) ranges from −196° C. to −20° C. for 12 hours to 72 hours.

2. The preparation method according to claim 1, wherein the tissue comprises tissue or from a human body or an animal.

3. The preparation method according to claim 2, wherein the tissue comprises cerebrum, heart, liver, spleen, lungs, kidneys, muscles, skin, fat, meninges, diaphragm, amnion, pericardium, heart valves, small intestine submucosa, blood vessels, tendons, ligaments, cartilage, esophagus, trachea, stomach, nerves, bladder, cornea and/or placenta.

4. The decellularized extracellular matrix tissue paper prepared by the preparation method according to claim 1.

5. The decellularized extracellular matrix tissue paper prepared by the preparation method according to claim 2.

6. The decellularized extracellular matrix tissue paper prepared by the preparation method according to claim 3.

7. A preparation method of decellularized extracellular matrix porcine heart tissue paper, comprising the following steps:

(1) preparing decellularized extracellular matrix materials, comprising:

washing a porcine heart tissue with water, and then slicing the tissue to a thickness of 1 mm, and placing the sliced tissue into a glass bottle;

disinfecting and sterilizing the washed sliced tissue with a 0.1% peroxyacetic acid;

washing the disinfected and sterilized tissue by adding sterilized water and shaking on a shaker until a solution containing the disinfected and sterilized tissue becomes clear;

further washing the disinfected and sterilized tissue with a 1% sodium dodecyl sulfate (SDS) solution while shaking on a shaker for 72 hours, and changing the SDS solution once every three hours, until the tissue becomes white;

washing the white tissue by adding sterilized water to remove residual SDS;

adding a Tris-HCL buffer with DNase and RNase to the washed tissue to form a mixture, and then shaking the mixture on a shaker at 37° C. and 100 rpm for 24 hours to remove DNA and RNA from the tissue; and washing the mixture with sterilized water to obtain porcine heart extracellular matrix material;

(2) preparing tissue paper, comprising:

placing 10 grams of the porcine heart extracellular matrix material from step (1) in 100 mL of distilled water to form a mixture;

homogenizing the mixture for 10 minutes to obtain a homogenate;

placing the homogenate on a flat-bottom filter screen having a diameter of 8 cm to filter out water from the obtained homogenate to obtain filtered homogenate, and air-drying the filtered homogenate on the flat-bottom filter screen at room temperature to obtain air-dried homogenate, wherein the filtering and air-drying are performed for a total of 48 hours;

freezing the filtered and air-dried homogenate at −80° C. for 4 hours to produce a frozen homogenate; and transferring the frozen homogenate to a freeze-dryer for freeze-drying to obtain porcine heart tissue paper;

(3) cross-linking the porcine heart tissue paper, comprising:

preparing 100 mL of 80% ethanol solution and adding1-ethyl-(3-dimethylaminopropyl) carbonyldiimine (EDC) and N-hydroxysuccinimide (NHS) at a mass ratio of 4:1 to the ethanol solution to prepare a cross-linking solution with a concentration of 0.3%;

immersing the porcine heart tissue paper into the cross-linking solution at 4° C. for 10 hours to obtain cross-linked porcine heart tissue paper; and removing the cross-linked porcine heart tissue paper from the cross-linking solution, and soaking and washing the removed cross-linked porcine heart tissue paper with sterilized water several times to remove residual cross-linking agents; and (4) freeze-drying the cross-linked porcine heart tissue paper, comprising:

freeze-drying the cross-linked porcine heart tissue paper obtained in step (3) by freezing at −20° C. for 12 hours, and then freeze-drying in a freeze dryer for 48 hours, to obtain the decellularized extracellular matrix porcine heart tissue paper.

* * * * *